(12) United States Patent
Paternuosto (10) Patent No.: US 7,909,850 B2
(45) Date of Patent: Mar. 22, 2011

(54) FORCEPS FOR MEDICAL USE

(75) Inventor: Mario I. Paternuosto, Angelo In Formis (IT)

(73) Assignee: Boston Scientific Scimed, Inc., Maple Grove, MN (US)

(*) Notice: Subject to any disclaimer, the term of this patent is extended or adjusted under 35 U.S.C. 154(b) by 1315 days.

(21) Appl. No.: 11/319,137

(22) Filed: Dec. 28, 2005

(65) Prior Publication Data
US 2006/0129185 A1  Jun. 15, 2006

Related U.S. Application Data

(63) Continuation of application No. 10/111,372, filed as application No. PCT/IB00/01532 on Oct. 24, 2000, now Pat. No. 7,118,586.

(30) Foreign Application Priority Data

Oct. 25, 1999 (IT) .................................. CE99A0004

(51) Int. Cl.
*A61B 17/00* (2006.01)

(52) U.S. Cl. ......... 606/205; 606/207; 600/562; 600/564

(58) Field of Classification Search .................. 606/114, 606/205, 206, 207, 208, 127, 128; 600/562, 600/564, 570; 220/4.21, 4.22, 4.23, 4.24, 220/4.25, 694, 735
See application file for complete search history.

(56) References Cited

U.S. PATENT DOCUMENTS

| | | |
|---|---|---|
| 30,471 A | 10/1860 | Dudley |
| 1,609,014 A | 11/1926 | Edward |
| 1,615,494 A | 1/1927 | Waring |
| 1,924,348 A | 8/1933 | Brown |
| 1,931,740 A | 10/1933 | Ryan |
| 2,115,298 A | 4/1938 | Brown |
| 2,131,780 A | 10/1938 | Storz |
| 2,258,287 A | 10/1941 | Grieshaber |
| 2,729,210 A | 1/1956 | Spencer |
| 2,751,908 A | 6/1956 | Wallace |
| 2,778,357 A | 1/1957 | Leibinger et al. |
| 3,590,808 A | 7/1971 | Muller |
| 3,683,892 A | 8/1972 | Harris |
| 3,844,272 A | 10/1974 | Banko |
| 3,889,657 A | 6/1975 | Baumgarten |
| 4,522,206 A | 6/1985 | Whipple et al. |
| 4,598,710 A | 7/1986 | Kleinberg et al. |
| 4,632,110 A | 12/1986 | Sanagi |
| 4,644,951 A | 2/1987 | Bays |
| 4,646,751 A | 3/1987 | Maslankam |
| 4,651,752 A | 3/1987 | Fuerst |

(Continued)

FOREIGN PATENT DOCUMENTS

DE  G 85 32 644.5  5/1986

(Continued)

*Primary Examiner* — (Jackie) Tan-Uyen T Ho
*Assistant Examiner* — Jonathan W Miles
(74) *Attorney, Agent, or Firm* — Finnegan, Henderson, Farabow, Garrett & Dunner LLP (57) ABSTRACT

Forceps having two-half shells are disclosed. Each half-shell includes a front rim and a base wall and is mounted on a support element in a manner such that the half-shells can adopt a first opened-out configuration and a second closed configuration. The forceps include at least one container element having a cavity for receiving a plurality of biopsy samples. The container element is preferably associated with one of the half-shells.

51 Claims, 4 Drawing Sheets

U.S. PATENT DOCUMENTS

| | | |
|---|---|---|
| 4,651,753 A | 3/1987 | Lifton |
| 4,656,999 A | 4/1987 | Storz |
| 4,662,371 A | 5/1987 | Whipple et al. |
| 4,669,471 A | 6/1987 | Hayashi |
| 4,676,249 A | 6/1987 | Arenas et al. |
| 4,712,545 A | 12/1987 | Honkanen |
| 4,721,116 A | 1/1988 | Schintgen et al. |
| 4,763,668 A | 8/1988 | Macek et al. |
| 4,785,825 A | 11/1988 | Romaniuk et al. |
| 4,815,460 A | 3/1989 | Porat et al. |
| 4,815,476 A | 3/1989 | Clossick |
| 4,817,630 A | 4/1989 | Schintgen et al. |
| 4,880,015 A | 11/1989 | Nierman |
| 4,887,612 A | 12/1989 | Esser et al. |
| 4,889,118 A | 12/1989 | Schwiegerling |
| 4,907,599 A | 3/1990 | Taylor |
| 4,936,312 A | 6/1990 | Tsukagoshi |
| 4,950,273 A | 8/1990 | Briggs |
| 4,953,559 A | 9/1990 | Salerno |
| 4,971,067 A | 11/1990 | Bolduc et al. |
| 4,986,279 A | 1/1991 | O'Neill |
| 4,986,825 A | 1/1991 | Bays et al. |
| 4,994,024 A | 2/1991 | Falk |
| 5,037,379 A | 8/1991 | Clayman et al. |
| 5,052,402 A | 10/1991 | Bencini et al. |
| 5,059,214 A | 10/1991 | Akopov et al. |
| 5,074,867 A | 12/1991 | Wilk |
| 5,082,000 A | 1/1992 | Picha et al. |
| 5,147,371 A | 9/1992 | Washington et al. |
| 5,148,813 A | 9/1992 | Bucalo |
| 5,152,778 A | 10/1992 | Bales, Jr. et al. |
| 5,161,542 A | 11/1992 | Palestrant |
| 5,171,256 A | 12/1992 | Smith et al. |
| 5,172,700 A * | 12/1992 | Bencini et al. ............... 600/564 |
| 5,176,687 A | 1/1993 | Hasson et al. |
| 5,183,052 A | 2/1993 | Terwilliger |
| 5,183,054 A | 2/1993 | Burkholder et al. |
| 5,188,118 A | 2/1993 | Terwilliger |
| 5,190,542 A | 3/1993 | Nakao et al. |
| 5,190,555 A | 3/1993 | Wetter et al. |
| 5,192,284 A | 3/1993 | Pleatman |
| 5,192,286 A | 3/1993 | Phan et al. |
| 5,195,533 A | 3/1993 | Chin et al. |
| 5,197,968 A | 3/1993 | Clement |
| 5,201,740 A | 4/1993 | Nakao et al. |
| 5,217,458 A | 6/1993 | Parins |
| 5,238,002 A | 8/1993 | Devlin et al. |
| 5,241,968 A | 9/1993 | Slater |
| 5,249,582 A | 10/1993 | Taylor |
| 5,251,641 A | 10/1993 | Xavier |
| 5,263,967 A | 11/1993 | Lyons, III et al. |
| 5,267,572 A | 12/1993 | Bucalo |
| 5,285,795 A | 2/1994 | Ryan et al. |
| 5,300,087 A | 4/1994 | Knoepfler |
| 5,316,013 A | 5/1994 | Striebel, II et al. |
| 5,330,502 A | 7/1994 | Hassler et al. |
| 5,341,815 A | 8/1994 | Cofone et al. |
| 5,342,389 A | 8/1994 | Haber et al. |
| 5,348,023 A | 9/1994 | McLucas |
| 5,352,184 A | 10/1994 | Goldberg et al. |
| 5,354,303 A | 10/1994 | Spaeth et al. |
| 5,366,467 A | 11/1994 | Lynch et al. |
| 5,368,597 A | 11/1994 | Pagedas |
| 5,373,854 A | 12/1994 | Kolozsi |
| 5,374,227 A | 12/1994 | Webb |
| 5,374,277 A | 12/1994 | Hassler |
| 5,383,888 A | 1/1995 | Zvenyatsky et al. |
| 5,385,570 A | 1/1995 | Chin et al. |
| 5,396,900 A | 3/1995 | Slater et al. |
| 5,419,220 A | 5/1995 | Cox |
| 5,423,854 A | 6/1995 | Martin et al. |
| 5,449,001 A | 9/1995 | Terwilliger |
| 5,465,731 A | 11/1995 | Bell et al. |
| 5,471,992 A | 12/1995 | Banik et al. |
| 5,476,099 A | 12/1995 | Robinson et al. |
| 5,482,054 A | 1/1996 | Slater et al. |
| 5,511,556 A | 4/1996 | DeSantis |
| 5,535,754 A | 7/1996 | Doherty |
| 5,538,008 A | 7/1996 | Crowe |
| 5,542,432 A | 8/1996 | Slater et al. |
| 5,558,100 A | 9/1996 | Cox |
| 5,560,373 A | 10/1996 | De Santis |
| 5,562,102 A | 10/1996 | Taylor |
| 5,564,436 A | 10/1996 | Hakky et al. |
| 5,569,299 A | 10/1996 | Dill et al. |
| 5,571,129 A | 11/1996 | Porter |
| 5,573,008 A | 11/1996 | Robinson et al. |
| 5,573,546 A * | 11/1996 | Nakao ........................... 606/205 |
| 5,595,185 A | 1/1997 | Erlich |
| 5,601,585 A | 2/1997 | Banik et al. |
| 5,613,499 A * | 3/1997 | Palmer et al. ................. 600/564 |
| 5,636,639 A | 6/1997 | Turturro et al. |
| 5,638,827 A | 6/1997 | Palmer et al. |
| 5,643,283 A | 7/1997 | Younker |
| 5,643,307 A | 7/1997 | Turkel et al. |
| 5,645,075 A | 7/1997 | Palmer et al. |
| 5,647,372 A | 7/1997 | Tovey et al. |
| 5,653,713 A | 8/1997 | Michelson |
| 5,662,671 A | 9/1997 | Barbut et al. |
| 5,669,394 A | 9/1997 | Bergey et al. |
| 5,681,324 A | 10/1997 | Kammerer et al. |
| 5,681,348 A | 10/1997 | Sato |
| 5,683,359 A | 11/1997 | Farkas et al. |
| 5,683,388 A | 11/1997 | Slater |
| 5,683,413 A | 11/1997 | Miyagi |
| 5,707,392 A | 1/1998 | Kortenbach |
| 5,720,754 A | 2/1998 | Middleman et al. |
| 5,735,289 A | 4/1998 | Pfeffer et al. |
| 5,746,216 A | 5/1998 | Turturro et al. |
| 5,746,740 A | 5/1998 | Nicholas |
| 5,759,187 A | 6/1998 | Nakao et al. |
| 5,762,069 A | 6/1998 | Kelleher et al. |
| 5,762,070 A | 6/1998 | Nagamatsu |
| 5,762,613 A | 6/1998 | Sutton et al. |
| 5,766,177 A | 6/1998 | Lucas-Dean et al. |
| 5,775,333 A | 7/1998 | Burbank et al. |
| 5,776,075 A | 7/1998 | Palmer |
| 5,779,646 A | 7/1998 | Koblish et al. |
| 5,779,648 A | 7/1998 | Banik et al. |
| 5,779,716 A | 7/1998 | Cano et al. |
| 5,795,308 A | 8/1998 | Russin |
| 5,797,957 A | 8/1998 | Palmer et al. |
| 5,807,276 A | 9/1998 | Russin |
| 5,807,277 A | 9/1998 | Swaim |
| 5,810,744 A | 9/1998 | Chu et al. |
| 5,810,876 A | 9/1998 | Kelleher |
| 5,820,630 A | 10/1998 | Lind |
| 5,823,971 A | 10/1998 | Robinson et al. |
| 5,840,043 A | 11/1998 | Palmer et al. |
| 5,840,044 A | 11/1998 | Dassa et al. |
| 5,843,000 A | 12/1998 | Nishioka et al. |
| 5,846,248 A | 12/1998 | Chu et al. |
| 5,848,978 A | 12/1998 | Cecchi |
| 5,853,374 A | 12/1998 | Hart et al. |
| 5,871,453 A | 2/1999 | Banik et al. |
| 5,893,876 A | 4/1999 | Turkel et al. |
| 5,895,361 A | 4/1999 | Turturro |
| 5,897,507 A | 4/1999 | Kortenbach et al. |
| 5,906,621 A | 5/1999 | Secrest et al. |
| 5,908,437 A | 6/1999 | Asano et al. |
| 5,919,206 A | 7/1999 | Gengler et al. |
| 5,928,161 A | 7/1999 | Krulevitch et al. |
| 5,928,164 A | 7/1999 | Burbank et al. |
| 5,944,673 A | 8/1999 | Gregoire et al. |
| 5,951,488 A | 9/1999 | Slater et al. |
| 5,957,932 A | 9/1999 | Bates et al. |
| 5,961,534 A | 10/1999 | Banik et al. |
| 5,964,716 A | 10/1999 | Gregoire et al. |
| 5,967,997 A | 10/1999 | Turturro et al. |
| 5,971,940 A | 10/1999 | Baker et al. |
| 5,980,468 A | 11/1999 | Zimmon |
| 6,007,546 A | 12/1999 | Snow et al. |
| 6,010,512 A | 1/2000 | Chu et al. |
| 6,013,095 A | 1/2000 | Ouchi |
| 6,019,733 A | 2/2000 | Farascioni |
| 6,019,758 A | 2/2000 | Slater |
| 6,019,770 A | 2/2000 | Christoudias |

| | | | | | | |
|---|---|---|---|---|---|---|
| 6,022,362 | A | 2/2000 | Lee et al. | 6,520,968 B2 | 2/2003 | Bates et al. |
| 6,036,698 | A | 3/2000 | Fawzi et al. | 6,527,781 B2 | 3/2003 | Bates et al. |
| RE36,666 | E | 4/2000 | Honkanen et al. | 6,530,891 B2 | 3/2003 | Miller |
| 6,050,955 | A | 4/2000 | Bryan et al. | 6,544,194 B1 | 4/2003 | Kortenbach et al. |
| 6,053,877 | A | 4/2000 | Banik et al. | 6,551,254 B2 | 4/2003 | Nishtalas et al. |
| 6,059,793 | A | 5/2000 | Pagedas | 6,554,850 B1 | 4/2003 | Ouchi et al. |
| 6,068,603 | A | 5/2000 | Suzuki | 6,561,988 B1 | 5/2003 | Turturro et al. |
| 6,071,233 | A | 6/2000 | Ishikawa et al. | 6,565,591 B2 | 5/2003 | Brady et al. |
| 6,071,248 | A | 6/2000 | Zimmon | 6,575,977 B1 | 6/2003 | Michelson |
| 6,074,408 | A | 6/2000 | Freeman | 6,589,252 B2 | 7/2003 | McGuckin, Jr. |
| 6,077,230 | A | 6/2000 | Gregoire et al. | 6,607,227 B1 | 8/2003 | Morton |
| 6,083,150 | A | 7/2000 | Aznoian et al. | 6,613,068 B2 | 9/2003 | Ouchi |
| 6,083,240 | A | 7/2000 | Ouchi | 6,620,111 B2 | 9/2003 | Stephens et al. |
| 6,093,195 | A | 7/2000 | Ouchi | 6,626,915 B2 | 9/2003 | Leveillee |
| 6,099,483 | A | 8/2000 | Palmer et al. | 6,632,182 B1 | 10/2003 | Treat |
| 6,099,534 | A | 8/2000 | Bates et al. | 6,673,092 B1 | 1/2004 | Bacher |
| 6,106,553 | A | 8/2000 | Feingold | 6,685,723 B1 | 2/2004 | Ouchi et al. |
| 6,110,127 | A | 8/2000 | Suzuki | 6,689,122 B2 | 2/2004 | Yamamoto |
| 6,123,678 | A | 9/2000 | Palmer et al. | 6,695,791 B2 | 2/2004 | Gonzalez |
| 6,129,683 | A | 10/2000 | Sutton et al. | 6,709,445 B2 | 3/2004 | Boebel et al. |
| 6,139,508 | A | 10/2000 | Simpson et al. | 6,736,781 B2 | 5/2004 | Lee |
| 6,142,955 | A | 11/2000 | Farascioni et al. | 6,740,106 B2 | 5/2004 | Kobayashi et al. |
| 6,142,956 | A | 11/2000 | Kortenbach et al. | 6,743,228 B2 | 6/2004 | Lee et al. |
| 6,142,957 | A | 11/2000 | Diamond et al. | 6,752,822 B2 | 6/2004 | Jespersen |
| 6,149,607 | A | 11/2000 | Simpson et al. | 6,792,663 B2 | 9/2004 | Krzyzanowski |
| 6,155,988 | A | 12/2000 | Peters | 6,805,699 B2 | 10/2004 | Shimm |
| 6,159,162 | A | 12/2000 | Kostylev et al. | 6,808,491 B2 | 10/2004 | Kortenbach et al. |
| 6,168,603 | B1 | 1/2001 | Leslie et al. | 2001/0000348 A1 | 4/2001 | Chu et al. |
| 6,171,315 | B1 | 1/2001 | Chu et al. | 2001/0009978 A1 | 7/2001 | Krueger et al. |
| 6,174,292 | B1 | 1/2001 | Kortenbach et al. | 2001/0047124 A1 | 11/2001 | Yamamoto |
| 6,174,318 | B1 | 1/2001 | Bates et al. | 2001/0056248 A1 | 12/2001 | Zimmon |
| 6,183,482 | B1 | 2/2001 | Bates et al. | 2002/0013595 A1 | 1/2002 | Yamamoto |
| 6,190,399 | B1 | 2/2001 | Palmer et al. | 2002/0022850 A1 | 2/2002 | McGuckin |
| 6,193,671 | B1 | 2/2001 | Turturro et al. | 2002/0029006 A1 | 3/2002 | Turturro et al. |
| 6,206,904 | B1 | 3/2001 | Ouchi | 2002/0065474 A1 | 5/2002 | Viola |
| 6,224,612 | B1 | 5/2001 | Bates et al. | 2002/0068944 A1 | 6/2002 | White et al. |
| 6,228,095 | B1 | 5/2001 | Dennis | 2002/0095100 A1 | 7/2002 | Lee et al. |
| 6,231,522 | B1 | 5/2001 | Voegele et al. | 2002/0111564 A1 | 8/2002 | Burbank et al. |
| 6,241,687 | B1 | 6/2001 | Voegele et al. | 2002/0120211 A1 | 8/2002 | Wardle et al. |
| 6,248,081 | B1 | 6/2001 | Nishtalas et al. | 2002/0143270 A1 | 10/2002 | Miller |
| 6,258,102 | B1 | 7/2001 | Pagedas | 2002/0156395 A1 | 10/2002 | Stephens et al. |
| 6,264,618 | B1 | 7/2001 | Landi et al. | 2002/0188220 A1 | 12/2002 | Krzyzanowski |
| 6,264,663 | B1 | 7/2001 | Cano | 2002/0193705 A1 | 12/2002 | Burbank et al. |
| 6,273,860 | B1 | 8/2001 | Kostylev et al. | 2002/0198466 A1 | 12/2002 | Alberico |
| 6,273,861 | B1 | 8/2001 | Bates et al. | 2003/0040681 A1 | 2/2003 | Ng et al. |
| 6,280,398 | B1 | 8/2001 | Ritchart et al. | 2003/0073928 A1 | 4/2003 | Kortenbach et al. |
| 6,280,451 | B1 | 8/2001 | Bates et al. | 2003/0097147 A1 | 5/2003 | Prestel |
| 6,283,924 | B1 | 9/2001 | Ouchi | 2003/0105402 A1 | 6/2003 | Lee |
| 6,299,630 | B1 | 10/2001 | Yamamoto | 2003/0120281 A1 | 6/2003 | Bates et al. |
| 6,309,404 | B1 | 10/2001 | Krzyzanowski | 2003/0125639 A1 | 7/2003 | Fisher et al. |
| 6,322,522 | B1 | 11/2001 | Zimmon | 2003/0163129 A1 | 8/2003 | Lee et al. |
| 6,328,701 | B1 | 12/2001 | Terwilliger | 2003/0191413 A1 | 10/2003 | Damarati |
| 6,331,165 | B1 | 12/2001 | Turturro et al. | 2003/0191464 A1 | 10/2003 | Kidooka |
| 6,350,266 | B1 | 2/2002 | White et al. | 2003/0212342 A1 | 11/2003 | Rudnick et al. |
| 6,368,290 | B1 | 4/2002 | Baska | 2003/0229292 A1 | 12/2003 | Hibner et al. |
| 6,375,661 | B2 | 4/2002 | Chu et al. | 2003/0229293 A1 | 12/2003 | Hibner et al. |
| 6,378,351 | B1 | 4/2002 | Ouchi et al. | 2004/0015165 A1 | 1/2004 | Kidooka |
| 6,383,196 | B1 | 5/2002 | Leslie et al. | 2004/0024333 A1 | 2/2004 | Brown |
| 6,383,197 | B1 | 5/2002 | Conlon et al. | 2004/0034310 A1 | 2/2004 | McAlister et al. |
| 6,387,102 | B2 | 5/2002 | Pagedas | 2004/0059345 A1 | 3/2004 | Nakao et al. |
| 6,409,678 | B1 | 6/2002 | Ouchi | 2004/0068291 A1 | 4/2004 | Suzuki |
| 6,409,733 | B1 | 6/2002 | Conlon et al. | 2004/0087872 A1 | 5/2004 | Anderson et al. |
| 6,419,640 | B1 | 7/2002 | Taylor | 2004/0087979 A1 | 5/2004 | Field et al. |
| 6,419,679 | B1 | 7/2002 | Dhindsa | 2004/0092967 A1 | 5/2004 | Sancoff et al. |
| 6,425,910 | B1 | 7/2002 | Hugueny et al. | 2004/0097829 A1 | 5/2004 | McRury et al. |
| 6,427,509 | B1 | 8/2002 | Ouchi et al. | 2004/0138587 A1 | 7/2004 | Lyons |
| 6,432,064 | B1 | 8/2002 | Hibner et al. | 2004/0199159 A1 | 10/2004 | Lee et al. |
| 6,436,054 | B1 | 8/2002 | Viola et al. | 2004/0220496 A1 | 11/2004 | Gonzalez |
| 6,440,085 | B1 | 8/2002 | Krzyzanowski | 2004/0254592 A1 | 12/2004 | DiCarlo et al. |
| 6,443,909 | B1 | 9/2002 | Ouchi | | | |
| 6,454,727 | B1 | 9/2002 | Burbank et al. | FOREIGN PATENT DOCUMENTS | | |
| 6,461,310 | B1 | 10/2002 | Palmer et al. | DE 8712328 U1 | 3/1988 | |
| 6,468,227 | B2 | 10/2002 | Zimmon | DE 8814560 U1 | 3/1989 | |
| 6,485,436 | B1 | 11/2002 | Truckai et al. | DE 3920706 A1 | 1/1991 | |
| 6,488,636 | B2 | 12/2002 | Bryan et al. | DE 4006673 A1 | 9/1991 | |
| 6,494,885 | B1 | 12/2002 | Dhindsa | DE 9211834 U1 | 4/1993 | |
| 6,514,197 | B1 | 2/2003 | Ouchi et al. | DE 68913909 T2 | 10/1994 | |
| 6,514,269 | B2 | 2/2003 | Yamamoto | DE 695 27 152 T2 | 6/1996 | |
| 6,517,498 | B1 | 2/2003 | Burbank et al. | DE 29614931 U1 | 3/1997 | |

| | | | | | | |
|---|---|---|---|---|---|---|
| DE | 69310072 | T2 | 11/1997 | JP | H10-137250 A | 5/1998 |
| DE | 69404526 | T2 | 12/1997 | JP | H10-137251 A | 5/1998 |
| DE | 69319668 | T2 | 12/1998 | JP | H11-076244 A | 3/1999 |
| DE | 10018674 | A1 | 11/2000 | JP | 3220164 B2 | 8/1999 |
| DE | 10048369 | A1 | 4/2001 | JP | H11-509132 T2 | 8/1999 |
| DE | 10048369 | C2 | 4/2001 | JP | H11-509459 T2 | 8/1999 |
| DE | 10051651 | A1 | 4/2001 | JP | H11-239582 A | 9/1999 |
| DE | 10056946 | A1 | 5/2001 | JP | 2000-279418 A | 10/2000 |
| DE | 10128553 | A1 | 1/2002 | JP | 2000-296131 A | 10/2000 |
| DE | 10123848 | A1 | 2/2002 | JP | 2001-095808 A | 4/2001 |
| DE | 10156313 | A1 | 6/2003 | JP | 2001-112763 A | 4/2001 |
| DE | 10316134 | A1 | 10/2003 | JP | 2001-137998 A | 5/2001 |
| DE | 10332613 | A1 | 2/2004 | JP | 3190029 82 | 7/2001 |
| EP | 0 207 829 | A1 | 1/1987 | JP | 2001-517468 A | 10/2001 |
| EP | 0 207 830 | A1 | 1/1987 | JP | 3220165 B2 | 10/2001 |
| EP | 0 279 358 | A2 | 8/1988 | JP | 2001-321386 A | 11/2001 |
| EP | 0 279 358 | B1 | 8/1988 | JP | 2002-011014 A | 1/2002 |
| EP | 0 380 874 | A1 | 8/1990 | JP | 2002-065598 A | 3/2002 |
| EP | 0 428 607 | A1 | 5/1991 | JP | 2003-093393 A | 4/2003 |
| EP | 0 367 818 | B1 | 3/1994 | JP | 2004-000424 A | 1/2004 |
| EP | 0 585 921 | A1 | 3/1994 | JP | 2004-049330 A | 2/2004 |
| EP | 0 593 929 | A1 | 4/1994 | WO | WO 89/10093 A1 | 11/1989 |
| EP | 0 592 243 | B1 | 4/1997 | WO | WO 90/01297 A1 | 2/1990 |
| EP | 0 621 009 | B1 | 7/1997 | WO | WO 94/13215 A2 | 6/1994 |
| EP | 0 573 817 | B1 | 7/1998 | WO | WO 94/26172 A1 | 11/1994 |
| EP | 0 902 647 | A1 | 3/1999 | WO | WO 94/26181 A1 | 11/1994 |
| EP | 0 910 284 | A1 | 4/1999 | WO | WO 95/20914 A1 | 8/1995 |
| EP | 1 028 650 | A1 | 8/2000 | WO | WO 96/19144 A1 | 6/1996 |
| EP | 1 161 183 | A1 | 12/2001 | WO | WO 96/24289 A2 | 8/1996 |
| EP | 0 798 982 | B1 | 6/2002 | WO | WO 97/41776 A1 | 11/1997 |
| EP | 1 240 870 | A1 | 9/2002 | WO | WO 97/41777 A1 | 11/1997 |
| EP | 1 252 863 | A1 | 10/2002 | WO | WO 98/06336 A1 | 2/1998 |
| EP | 1 312 313 | A1 | 5/2003 | WO | WO 98/35615 A1 | 8/1998 |
| EP | 1 348 378 | A1 | 10/2003 | WO | WO 99/07287 A1 | 2/1999 |
| EP | 1 371 332 | A1 | 12/2003 | WO | WO 99/15073 A1 | 4/1999 |
| EP | 1 001 706 | B1 | 3/2004 | WO | WO 99/20096 A2 | 4/1999 |
| EP | 1 432 360 | A2 | 6/2004 | WO | WO 99/53851 A1 | 10/1999 |
| JP | S62-049838 | A | 3/1987 | WO | WO 00/01304 A1 | 1/2000 |
| JP | H09-215747 | A | 8/1987 | WO | WO 00/07502 A1 | 2/2000 |
| JP | S62-176438 | A | 8/1987 | WO | WO 00/33743 A1 | 6/2000 |
| JP | H03-139340 | A | 6/1991 | WO | WO 00/54658 A1 | 9/2000 |
| JP | H04-307050 | A | 10/1992 | WO | WO 01/30242 A1 | 5/2001 |
| JP | H05-220157 | A | 8/1993 | WO | WO 02/062226 A1 | 8/2002 |
| JP | H05-237120 | A | 9/1993 | WO | WO 02/062227 A1 | 8/2002 |
| JP | H06-030942 | A | 2/1994 | WO | WO 03/022157 A2 | 3/2003 |
| JP | H06-114063 | A | 4/1994 | WO | WO 03/024300 A2 | 3/2003 |
| JP | H06-189966 | A | 7/1994 | WO | WO 03/028557 A1 | 4/2003 |
| JP | H06-197906 | A | 7/1994 | WO | WO 03/082119 A1 | 10/2003 |
| JP | H08-206120 | A | 8/1996 | WO | WO 03/082122 A1 | 10/2003 |
| JP | H08-224242 | A | 9/1996 | WO | WO 03/105674 A2 | 12/2003 |
| JP | H09-508561 | T2 | 9/1997 | WO | WO 2004/010874 A1 | 2/2004 |
| JP | H09-276282 | A | 10/1997 | | | |
| JP | 10-099342 | A | 4/1998 | * cited by examiner | | |
| JP | H10-137246 | A | 5/1998 | | | |

FORCEPS FOR MEDICAL USE

CROSS-REFERENCE TO RELATED APPLICATIONS

This is a continuation of U.S. patent application Ser. No. 10/111,372, filed Sep. 10, 2002, now pending, which is a national stage of PCT International Application No. 01/PCT/IB00/01532 A1, filed Oct. 24, 2000, now U.S. Pat. No. 7,118,586, and claims priority to Italian Application No. CE99A000004, filed Oct. 25, 1999, the entirety of all of which are incorporated herein by reference.

The present invention relates to forceps for medical use, in particular for biopsy, for example, for endoscopic biopsy, laparoscopy, gynaeocological applications and the like.

More specifically, a conventional forceps of this type comprises two half-shells, each of which has a front rim and a base wall, and which are mounted on a support element in a manner such that they can adopt a first, opened-out configuration and a second, closed configuration.

In use, for example, during digestive endoscopy, the forceps is passed through the operating duct of an endoscope in the closed configuration and is brought into contact with the internal mucosa of the organ (for example, the oesophagus, stomach, duodenum, or colon) to be biopsied.

Once the forceps has been positioned correctly, the half-shells are opened and then closed so as to cut off a sample of the mucosa which remains held between them. Given the intrinsically limited nature of the space available, the closed half-shells can hold at most 2-3 biopsy samples.

However, pathological conditions frequently occur in which the number of samples taken has to be greater, as with gastric ulcers, or dysplasia or neoplasia in ulcerative pancolitis, which is a serious chronic disease of the colon.

In these cases, each time the space inside the half-shells is filled with biopsy samples, the forceps has to be withdrawn through the endoscope duct, emptied and reintroduced to the operation site. A large amount of wear and deformation of the duct thus takes place, with the risk of rupture and consequent infiltration of liquid which may cause very serious damage to the endoscope.

Another problem connected with the need to perform a plurality of introductions and withdrawals of the forceps consists of the long duration of this procedure which is due, among other things, to the need to empty the half-shells. Owing to the small size of the samples taken, this operation in fact takes the operator a considerable amount of time. In operative practice, however, the time available—in certain conditions, for example, with markedly intolerant patients who are unable to take sedatives—may be very limited, so that the use of conventional forceps is difficult.

To prevent the problems of the prior art mentioned above, the subject of the present invention is forceps of the type described at the beginning of the present description and characterized in that it has at least one container element having a cavity for receiving a plurality of biopsy samples.

The forceps of the invention can therefore be used to take all of samples necessary for a given pathological condition, in succession, by performing only one introduction and withdrawal, thus considerably reducing the time required for the operation, as well as the wear of the endoscope duct.

Moreover, during the withdrawal stage, the container element keeps the biopsy samples isolated from the duct, which has the advantage of preventing any mixing with impurities or with any scraps remaining from other samples taken, which may be present therein.

Further advantages and characteristics of the present invention will become clear from the following detailed description, provided by way of non-limiting example with reference to the appended drawings, in which.

A biopsy forceps, for example, for endoscopic biopsy, comprises (FIGS. 1-3) two half-shells $10a$, $10b$ each having a front rim 12 and a base wall 14. The half-shells $10a$, $10b$ are mounted in conventional manner, for example, on a support element 16 so that they can adopt a first, opened-out configuration (shown in the drawings) and a second, closed configuration in which the rims 12 of the two half-shells $10a$, $10b$ are in contact with one another.

Figures 1, 2, 3:
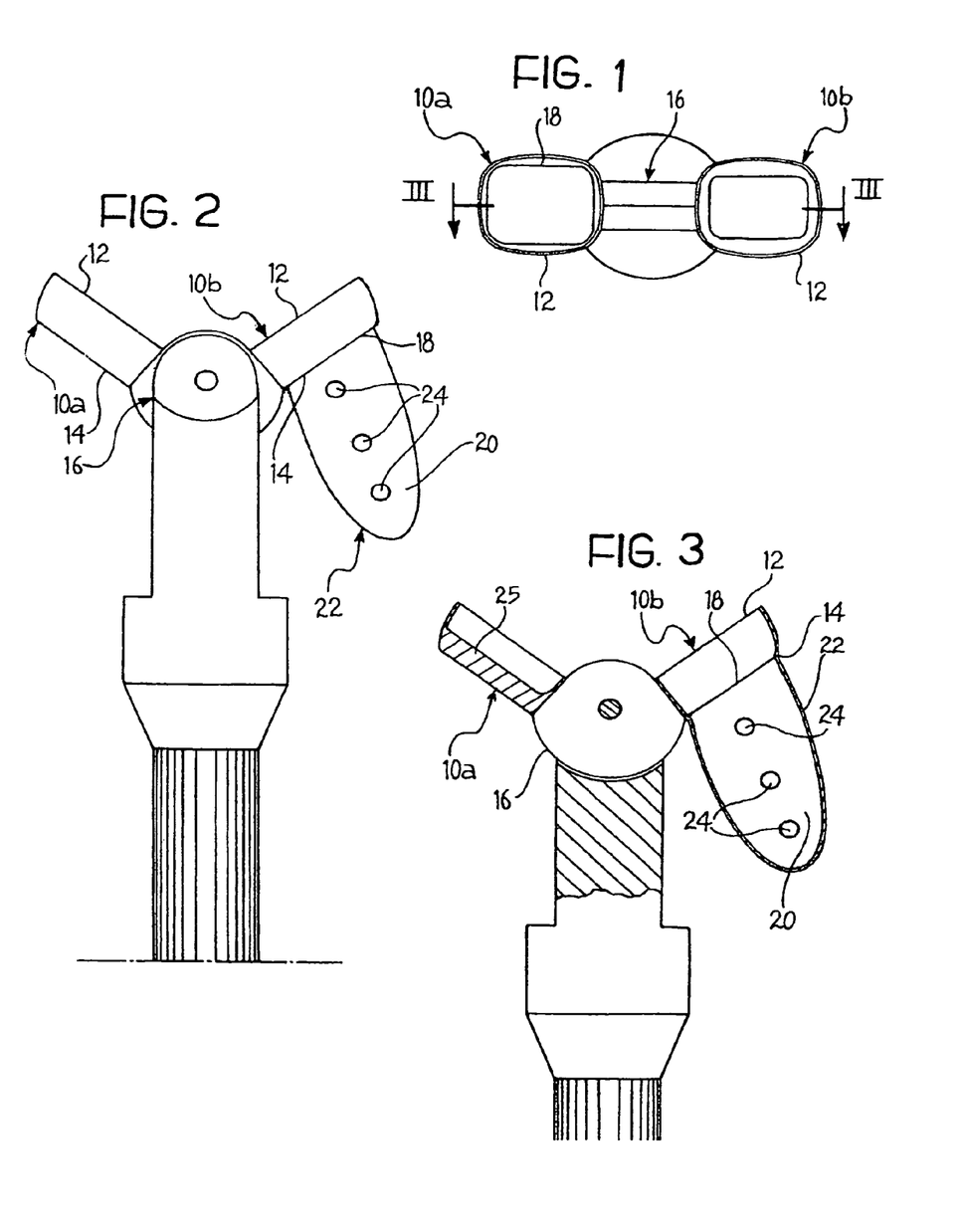
FIG. 1 is a schematic plan view of a forceps of the invention.
FIG. 2 is a front elevational view of the forceps of FIG. 1.
FIG. 3 is a section view taken on the line III-III of FIG. 1.
Figure 4:
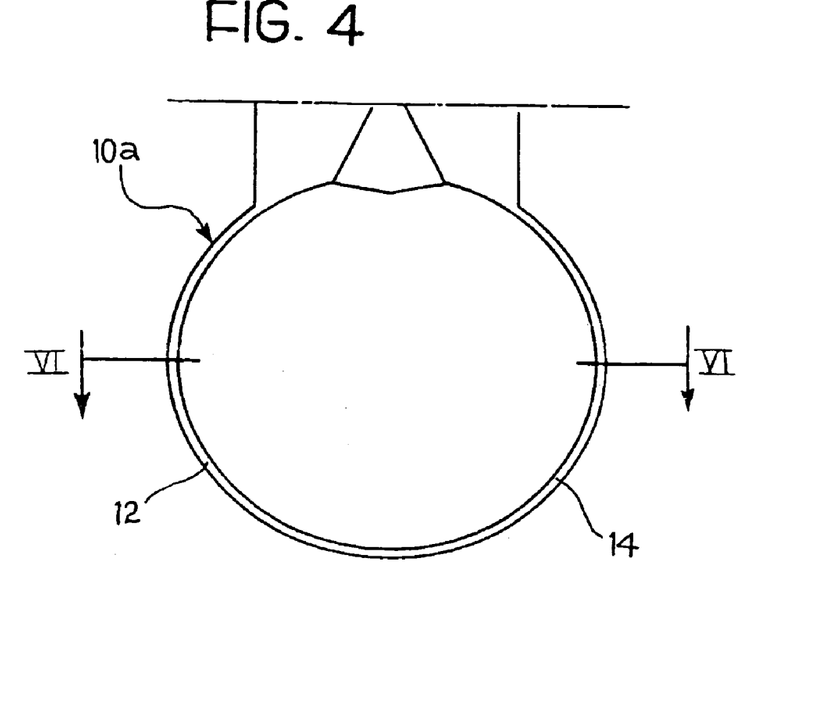
FIGS. 4 and 5 are respective plan views of each of the two half-shells of a forceps constituting an alternative embodiment of the invention.

The half-shell $10b$ has, in its base wall 14, a hole 18 which communicates with the cavity 20 inside a beaker-shaped container element 22 associated therewith and having a plurality of through-openings 24 in its walls.

The material constituting the element 22 is not critical within the scope of the present invention and may be selected, without particular limitations, from those suitable for use in the medical field.

The half-shell $10a$, on the other hand, is filled up to approximately a third of its height with filling material 25.

In use, the forceps is first of all passed through an endoscope duct (not shown in the drawings), with the half-shells $10a$, $10b$ in the closed configuration, until the forceps is in the desired location close to the internal mucosa of the organ to be biopsied. Here, the half-shells $10a$, $10b$ are opened out and closed again several times in succession so as to cut off a corresponding number of biopsy samples.

As these samples are taken one by one, they are urged towards the base of the container element 22 by the pressure exerted by the half-shell $10a$.

The openings 24 allow air and any organic liquids which remain trapped in the cavity 20 of the element 22 to be discharged, further facilitating the movement of the biopsy samples inside the element 22.

Upon completion of the cutting of the samples, the half-shells $10a$, $10b$ are closed again and the forceps, with its container element 22, can be withdrawn through the endoscope duct. The biopsy samples which are enclosed inside the cavity 20 do not therefore have any substantial contact with the duct, which could constitute a potential source of histological contamination.

FIGS. 4 to 7 show an alternative embodiment of the half-shells of a biopsy forceps according to the invention, which half-shells can be mounted on a support element in a manner similar to that described with reference to FIGS. 1-3.

In this embodiment, the half-shell $10a$ with which the container element 20 is not associated has (FIGS. 4 and 6) a base wall 14 having a central portion 26 which is raised substantially to the level of the rim 12, and an annular, recessed, peripheral portion 28.

The half-shell $10b$, on the other hand, (FIGS. 5 and 7) has, in its base wall 14, the hole 18 in which the end of the beaker-shaped container element 22 is fixed by means of an annular layer of adhesive 30, this end being open and having a restricted neck. The internal cavity 20 of the container element 22 thus constitutes a continuation of the space inside the half-shell 10b.

Figure 5:
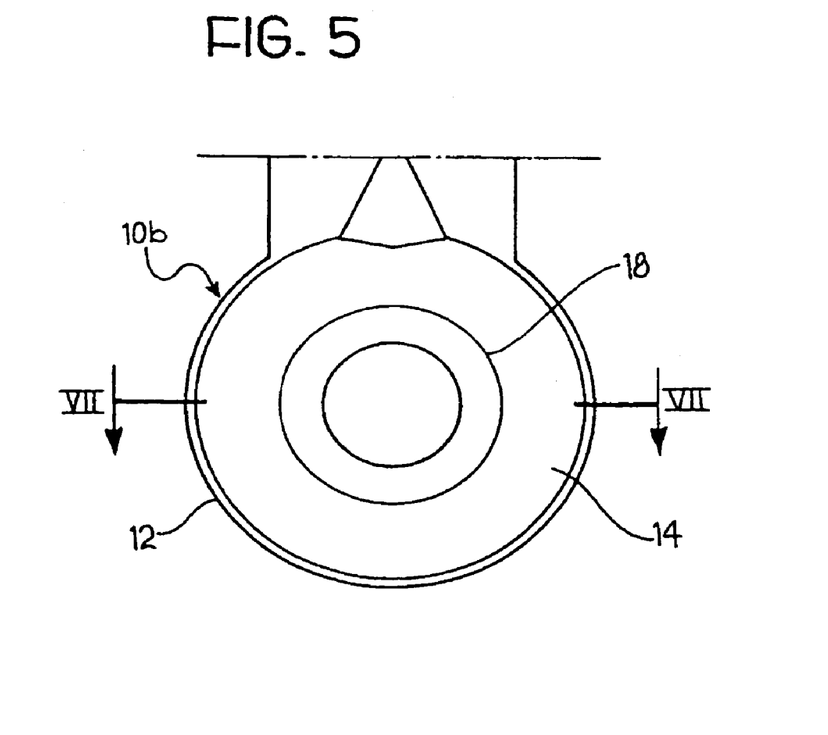
Figure 6:
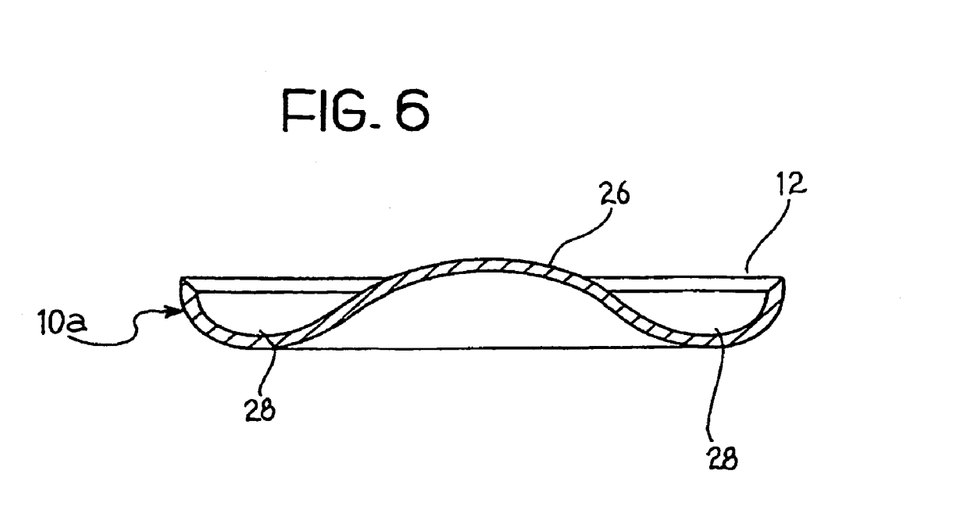
FIG. 6 is a section taken on the line VI-VI of FIG. 4.
Figure 7:
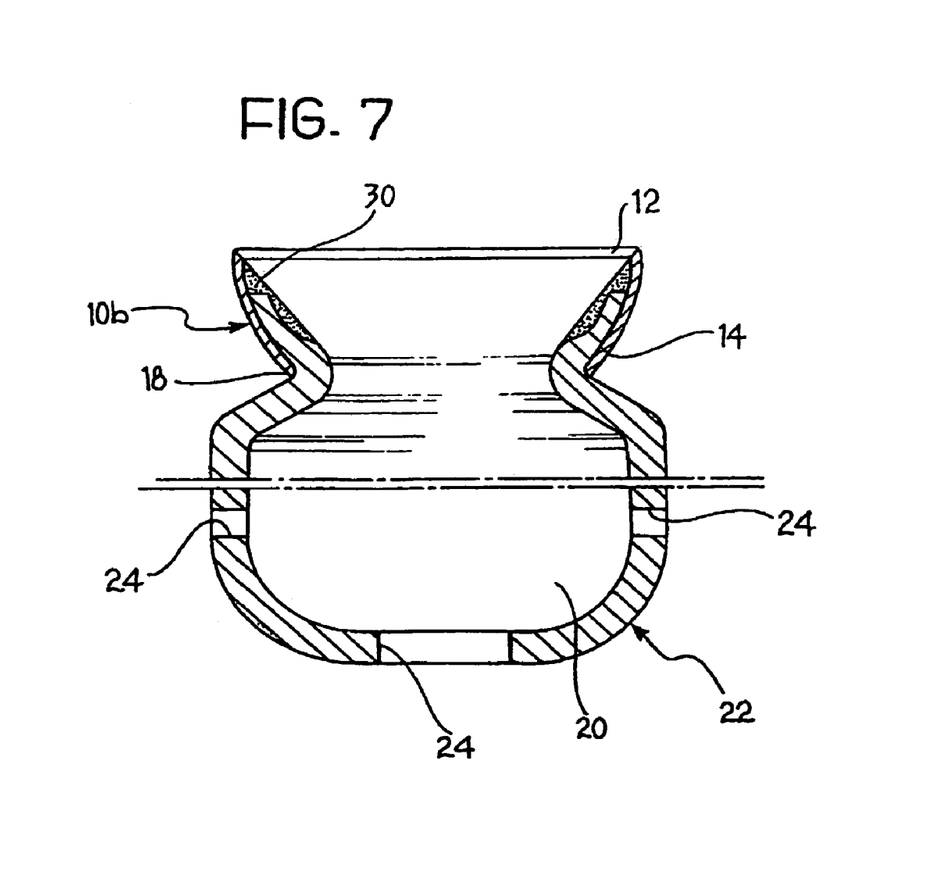
FIG. 7 is a section view taken on the line VII-VII of FIG. 5, and FIGS. 8 and 9 are views corresponding to FIGS. 5 and 7, respectively, of a further embodiment of a detail of a forceps of the invention.

The container element 22 also has openings 24 in its base and side walls.

The principle of the operation of the forceps having the half-shells just mentioned is substantially similar to that described with reference to FIGS. 1-3. The particular shape of the half-shell 10a enables a greater pressure to be exerted on the biopsy samples, directing them towards the cavity 20 of the element 22.

Figure 8:
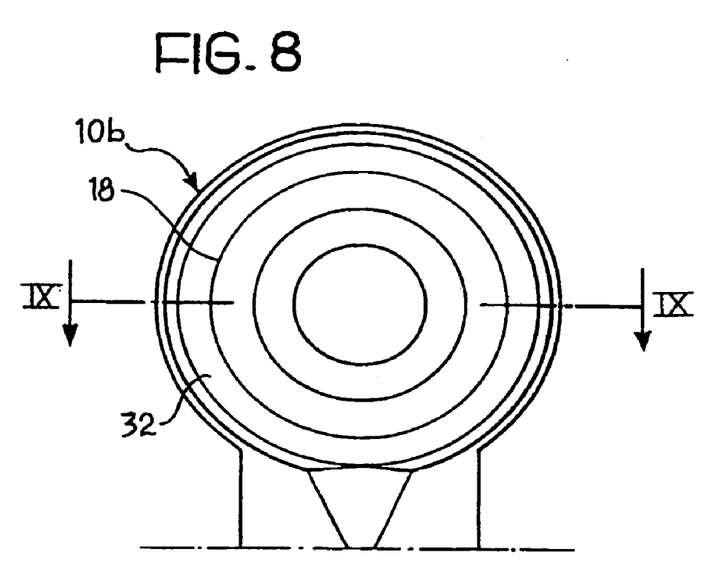
Figure 9:
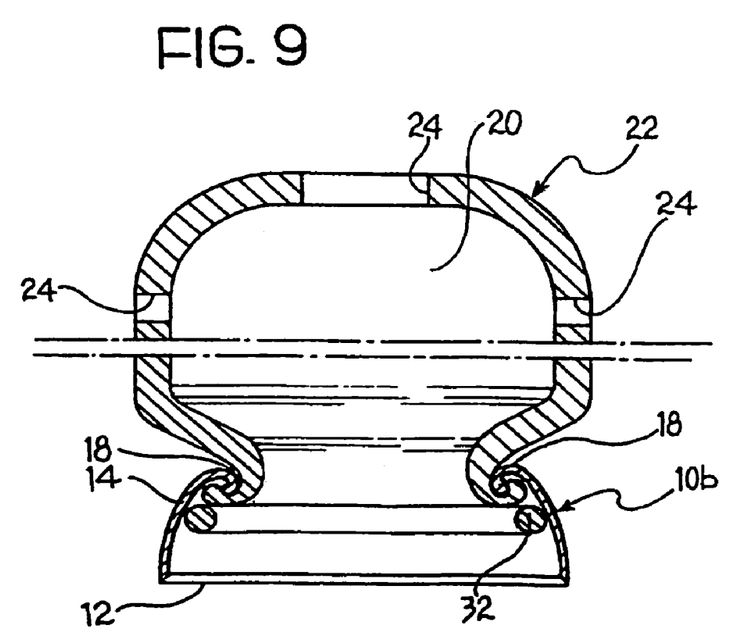

FIGS. 8 and 9 show a variant of the fixing of the container element 22 to the half-shell 10b, which is an alternative to the use of the above-described layer of adhesive. In this case, the open end of the element 22 has a hooked rim for engaging a rim of complementary shape of the hole 18 of the half-shell 10b. This engagement is preferably secured by a mechanical element such as a spring ring 32.

Naturally, the principle of the invention remaining the same, the details of construction and forms of embodiment may be varied widely with respect to those described purely by way of example, without thereby departing from its scope. In particular, both of the half-shells may have their own container elements and/or may have, independently of one another, any shape, for example, with a toothed or serrated rim. The container element in turn may have substantially any shape and/or length and/or may be in the form of a net engaged directly on the rim of the associated half-shell. Moreover, the container element may equally well be secured on the respective half-shell immovably, or releasably.

The invention claimed is:

1. A medical device, comprising:
a first half-shell and a second half-shell, each of the first half-shell and the second half-shell having a front rim and a base wall, the first half-shell and the second half-shell each being mounted on a support element in a manner such that the first and the second half-shells can adopt a first, open configuration and a second, closed configuration in which the front rim of the first half-shell contacts the front rim of the second half-shell without the front rim of the first half-shell entering a cavity of the second half-shell or the front rim of the second half-shell entering a cavity in the first half-shell, the first half-shell including a hole in the base wall configured to pass a biopsy sample; and
a container element associated with the first half-shell, the container element having an open end for receiving the biopsy sample into a cavity sized to contain a plurality of biopsy samples, the open end corresponding in size to the hole in the base wall of the first half-shell,
wherein the first half-shell has a configuration different from a configuration of the second half-shell, in both the open and closed configurations.

2. The medical device of claim 1, wherein the hole communicates with the cavity of the container element associated with the first half-shell.

3. The medical device of claim 1, wherein the container element is beaker-shaped and is fixed in the hole such that the cavity constitutes a continuation of a space inside the first half-shell.

4. The medical device of claim 3, wherein the container element includes a top portion and a bottom portion, the top portion being fixed to the base wall defining the hole in the first half-shell, and the bottom portion extending away from the first half-shell.

5. The medical device of claim 1, wherein the open end of the container element is fixed to the first half-shell by an annular layer of adhesive.

6. The medical device of claim 1, wherein the open end of the container element includes a hooked rim for engaging a rim of the hole of the first half-shell.

7. The medical device of claim 6, wherein the engagement of the hooked rim of the open end of the container element with the rim of the hole of the first half-shell is secured by a mechanical element.

8. The medical device of claim 7, wherein the mechanical element is a spring ring.

9. The medical device of claim 6, wherein the rim of the hole of the first half-shell is a complementary shape of the hooked rim of the container element.

10. The medical device of claim 1, wherein the container element is beaker-shaped and includes a container base and side walls, and has at least one opening in the container base or in the side walls.

11. The medical device of claim 10, wherein the container element has a plurality of openings in the container base and in the side walls.

12. The medical device of claim 11, wherein a length of an outer wall of the container element between adjacent holes is greater than a largest dimension of each of the plurality of holes.

13. The medical device of claim 11, wherein the container element includes a plurality of holes, and wherein a length of an outer wall of the container element extending between adjacent holes is greater than a largest dimension of each of the plurality of holes.

14. The medical device of claim 1, wherein at least a portion of the container element is completely encircled by the base wall of the first half-shell.

15. The medical device of claim 1, wherein the hole is configured to pass the plurality of biopsy samples therethrough.

16. The medical device of claim 1, wherein the first and second half-shells are configured to take biopsy samples.

17. The medical device of claim 1, wherein the container element includes an opening for discharging fluid from the cavity.

18. The medical device of claim 1, wherein an interior surface shape of the first half-shell is different than an interior surface shape of the second half-shell.

19. The medical device of claim 1, wherein an interior surface of the second half-shell includes a raised portion.

20. The medical device of claim 19, wherein the raised portion is a central portion raised to the front rim of the second half-shell.

21. The medical device of claim 1, wherein the configuration of the first half-shell and the second half-shell differ by the hole in the base wall of the first half-shell.

22. The medical device of claim 1, wherein the second half-shell is filled up to approximately a third of its height with filling material.

23. The medical device of claim 1, wherein the container element has substantially the same profile before and after receiving the plurality of biopsy samples.

24. The medical device of claim 1, wherein the container element has substantially the same profile before and after receiving the biopsy samples.

25. A medical device, comprising:
a support element;
a first half-shell supported by the support element;

a second half-shell supported by the support element, the first and second half-shells being operatively configured to open and close to take biopsy samples; and a container element affixed to the first half-shell, the container element having a first opening to a cavity for receiving the biopsy samples and a second opening for discharging fluid from the cavity, wherein a portion of the container element is shaped to retain the biopsy samples in the cavity of the container element, and wherein an interior surface shape of the first half-shell is different than an interior surface shape of the second half-shell, wherein, when the first half-shell and second half-shell are closed, a front rim of the first half-shell contacts a front rim of the second half-shell without the front rim of the first half-shell entering a cavity of the second half-shell or the front rim of the second half-shell entering a cavity of the first half-shell.

26. The medical device of claim 25, wherein the container element is beaker-shaped with the portion of the container element having a restrictive neck.

27. The medical device of claim 2, wherein the portion of the container element is adjacent the first opening to the cavity of the container element.

28. The medical device of claim 25, wherein the portion of the container element defines a restriction smaller than the first opening to the cavity of the container element.

29. The medical device of claim 25, wherein the second opening is at an end of the container element substantially opposite to the first opening.

30. The medical device of claim 25, wherein the first half-shell includes a hole which communicates with the first opening to the cavity of the container element affixed to the first half-shell.

31. The medical device of claim 30, wherein the hole is configured to pass the biopsy samples therethrough.

32. The medical device of claim 25, wherein the cavity of the container element is in communication with a space inside the first half-shell.

33. The medical device of claim 25, wherein the second half-shell includes a protrusion configured to push a biopsy sample into the cavity of the container element.

34. The medical device of claim 25, wherein an interior surface of the second half-shell includes a raised portion.

35. The medical device of claim 34, wherein the raised portion extends to the front rim of the second half-shell.

36. The medical device of claim 25, wherein the container element includes a top portion and a bottom portion, the top portion of the container element being fixed to the base wall defining the hole in the first half-shell, and the bottom portion extending away from the first half-shell.

37. A medical device, comprising:
a first half-shell and a second half-shell, each of the first half-shell and the second half-shell having a front rim and a base wall, the first half-shell and the second half-shell each being mounted on a support element in a manner such that the first and second half-shells can adopt a first, open configuration and a second, closed configuration in which the front rim of the first half-shell contacts the front rim of the second half-shell without the front rim of the first half-shell entering a cavity of the second half-shell or the front rim of the second half-shell entering a cavity of the first half-shell, the first half-shell including a hole in the base wall configured to pass a biopsy sample; and a container element associated with the first half-shell, the container element having an open end for receiving the biopsy sample into a cavity of the container element, and the container element having a restrictive portion for retaining a plurality of biopsy samples in the cavity, wherein a concavity of the first half-shell has a shape different than a shape of a concavity of the second half-shell.

38. The medical device of claim 37, wherein the restrictive portion is adjacent the open end.

39. The medical device of claim 37, wherein the restrictive portion is a restrictive neck, and the restrictive neck is smaller than the open end of the container element.

40. The medical device of claim 37, wherein the container element is fixed in the hole such that the cavity constitutes a continuation of a space inside the first half-shell.

41. The medical device of claim 40, wherein the container element includes a top portion and a bottom portion, the top portion being fixed to the base wall defining the hole in the first half-shell, and the bottom portion extending away from the first half-shell.

42. The medical device of claim 37, wherein the open end corresponds in size to the hole in the base wall of the first half-shell.

43. The medical device of claim 42, wherein at least a portion of the container element is completely encircled by the base wall.

44. The medical device of claim 37, wherein a rim of the hole in the base wall of the first half-shell is a complementary shape of the open end of the container element.

45. The medical device of claim 37, wherein the container element includes a container base and side walls, and has at least one opening in the container element base or in the side walls.

46. The medical device of claim 45, wherein the container element has a plurality of openings in the container base and in the side walls.

47. The medical device of claim 46, wherein a length of an outer wall between adjacent holes of the plurality of holes is greater than a largest dimension of each of the plurality of holes.

48. The medical device of claim 45, wherein the at least one opening is in the container base substantially opposite the open end.

49. The medical device of claim 37, wherein the second half-shell includes a protrusion configured to push a biopsy sample beyond the restrictive portion into the cavity.

50. The medical device of claim 37, wherein the base wall of the second half-shell includes a raised portion extending into the concavity of the second half-shell.

51. The medical device of claim 37, wherein the container element has substantially the same profile before and after receiving the plurality biopsy samples.

* * * * *